(12) United States Patent
You et al.

(10) Patent No.: US 12,303,543 B2
(45) Date of Patent: May 20, 2025

(54) COMPOSITION FOR PREVENTING OR TREATING GASTRITIS OR PEPTIC ULCER

(71) Applicant: CHONG KUN DANG PHARMACEUTICAL CORP., Seoul (KR)

(72) Inventors: Jaehoon You, Yongin-si (KR); Jong Lae Lim, Yongin-si (KR)

(73) Assignee: CHONG KUN DANG PHARMACEUTICAL CORP., Seoul (KR)

( * ) Notice: Subject to any disclaimer, the term of this patent is extended or adjusted under 35 U.S.C. 154(b) by 0 days.

(21) Appl. No.: 18/509,499

(22) Filed: Nov. 15, 2023

(65) Prior Publication Data

US 2024/0082337 A1    Mar. 14, 2024

Related U.S. Application Data

(62) Division of application No. 17/520,866, filed on Nov. 8, 2021, now Pat. No. 11,918,618, which is a division of application No. 16/466,353, filed as application No. PCT/KR2017/012349 on Nov. 2, 2017, now abandoned.

(30) Foreign Application Priority Data

Jan. 11, 2017  (KR) .................... 10-2017-0004418

(51) Int. Cl.
*A61K 36/00*   (2006.01)
*A23L 33/105*  (2016.01)
*A61K 36/54*   (2006.01)

(52) U.S. Cl.
CPC ............ *A61K 36/54* (2013.01); *A23L 33/105* (2016.08)

(58) Field of Classification Search
CPC ....................................................... A61P 1/04
See application file for complete search history.

(56) References Cited

FOREIGN PATENT DOCUMENTS

CN       102099028 A   *   6/2011   ........... A61K 31/353

\* cited by examiner

*Primary Examiner* — Qiuwen Mi
(74) *Attorney, Agent, or Firm* — LEX IP MEISTER, PLLC

(57) ABSTRACT

The present invention relates to a pharmaceutical or food composition comprising *Cinnamomum cassia* pretreated extract exhibiting an excellently enhanced pharmacological effect than *Cinnamomum cassia* extract prepared by a conventional common extraction method of *Cinnamomum cassia* and extract prepared with *Cinnamomum cassia* single herb medicine, or a method for preventing, improving or treating gastritis or peptic ulcer using the composition. In addition, the present invention relates to a preparation method of *Cinnamomum cassia* pretreated extract which is characterized by pretreating *Cinnamomum cassia* with a non-polar solvent and extracting it with a polar solvent.

1 Claim, 2 Drawing Sheets

[FIG. 1]
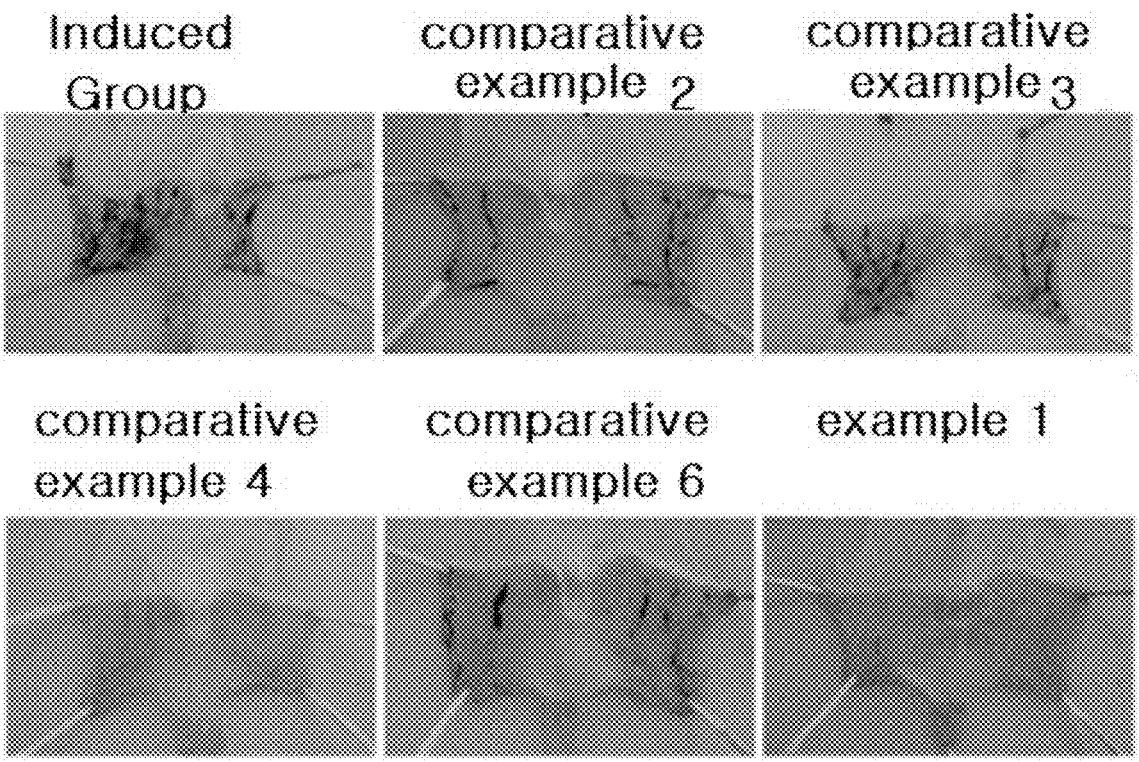

[FIG. 2]
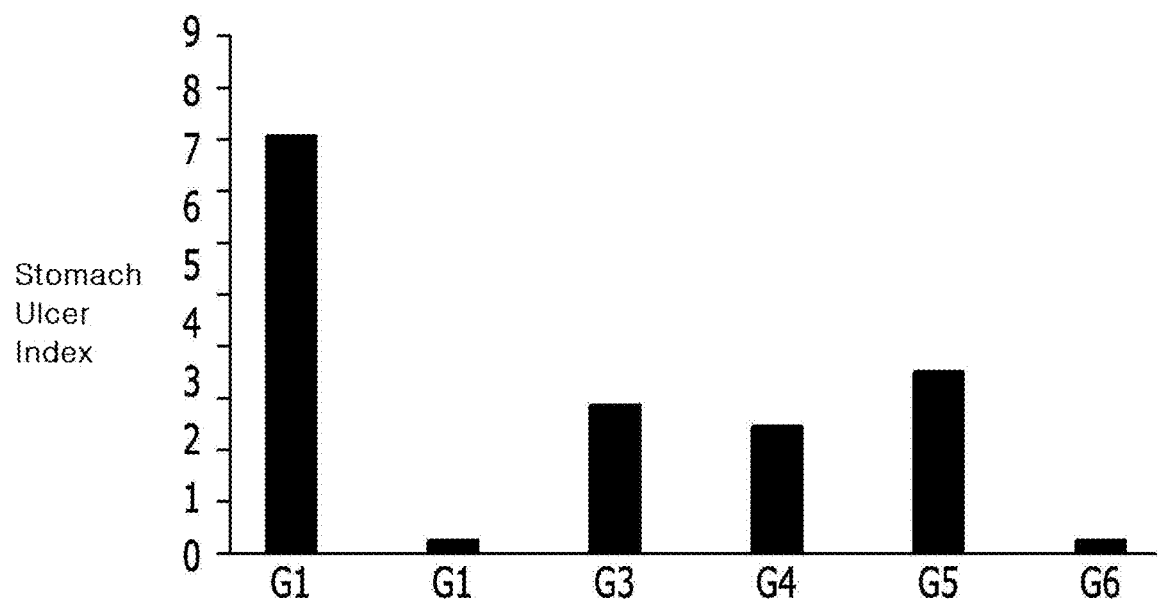
G1: Induced Group, G2: Comparative Example 4,
G3: Comparative Example 6, G4: Comparative Example 2,
G5: Comparative Example 6, G6: Example 1

COMPOSITION FOR PREVENTING OR TREATING GASTRITIS OR PEPTIC ULCER

TECHNICAL FIELD

The present invention relates to an enhanced composition capable of preventing or treating gastritis or peptic ulcer such as stomach ulcer. More specifically, the present invention relates to a composition for treating gastritis or stomach ulcer comprising *Cinnamomum cassia* extract, showing an excellently enhanced pharmacological effect than *Cinnamomum cassia* extract prepared by a conventional common extraction method of *Cinnamomum cassia* and extract prepared with *Cinnamomum cassia* single herb medicine, and a preparation method thereof.

BACKGROUND ART

Stomach is a part of digestive tract, and is a part inflated as a pocket between esophagus and small intestine (duodenum), and it is an organ which stores food entered through esophagus and breaks down it to facilitate digestion, and controls to send food to duodenum and is harmonized with secretion of digestive enzymes, thereby allowing efficient digestion and absorption. Factors that adversely affect a person's gastrointestinal function are extremely diverse in nature and can occur in the upper gastrointestinal tract, the lower gastrointestinal tract or both, and include a wide range of gastrointestinal disorders including genetic, physiological, environmental and mental factors. The representative diseases of the upper gastrointestinal tract are gastritis and peptic ulcer including stomach ulcer and duodenal ulcer. Gastritis presents damage and inflammation of stomach mucosa, and stomach ulcer means when such damage penetrates the mucosa and invades submucosa tissue and muscle layer. In addition, duodenal ulcer is ulcer occurred in duodenum and is also called peptic ulcer by collectively calling stomach ulcer and duodenal ulcer. These gastritis and peptic ulcer have been known to be occurred by imbalance of gastric acid, anti-inflammatory drug and bacterial inflammation called offensive factors, and mucus, cell regeneration, alkali secretion and so on called defensive factors.

Antacids which neutralize excess secreted gastric acid, histamine antagonists for inhibition of acid secretion, proton pump inhibitors, anticholinergics, stomach mucosa protectants increasing resistance of stomach intimae to the digestive solution and helping recovery, and the like are mainstreams for treatments of gastritis and peptic ulcer, and recently, there has been a drug treatment for prescribing the above drug and antibiotics in combination to remove *Helicobacter pylori*. The characteristics of antacids are rapid acting, and defensing damage of stomach mucosa by gastric acid by neutralizing gastric acid by raising pH in stomach. However, it affects the gastrointestinal tract smooth muscles by administration of inorganic materials, and thereby it may cause constipation or diarrhea, or cause allergic rejection.

Cimetidine is a representative of inhibitors of histamine receptor blocking secretion widely used for peptic ulcer, and there are ranitidine, famotidine, roxatidine, and the like as its derivatives, but they block histamine receptors in stomach mucosa and therefore histamine molecules act to prevent stomach cells from secreting acid. It shows an excellent anti-ulcer effect in clinical practice, but there is a disadvantage of high recurrence rate, since it is easily damaged by offensive factors such as gastric acid and the like after drug administration cessation, as cured regenerated mucosa and submucosa tissue have a week structure compared to normal tissue. In addition, ranitidine also has a disadvantage in that it is not effective for diseases such as acute gastritis caused by ethanol, and therefore the stomach mucosa protecting ability is not good.

As relatively recently developed proton pump inhibitors, there are omeprazole and lansoprazole and the like, and they are known to exhibit a strong acid secretion inhibitory effect by inhibiting acid secretion at the final stage from gastric wall cells, but it has a high recurrence rate and side effects such as diarrhea, fever, headache, fatigue and so on have been reported.

Stomach mucosa protectants are known to have a disadvantage in that it generally requires a long-term treatment and has a large dosage, but regenerated mucosa is recovered similarly to the normal different from offensive factor inhibitors.

*Helicobacter pylori* that is a type of bacteria inhabiting stomach is known as a representative cause of recurrence of peptic ulcer. *Helicobacter pylori* is a gram-negative *bacillus* that inhabits stomach mucosa epithelial intercellular junctions and causes chronic stomach ulcer, and treatment has been carried out to eradicate it and many achievements have been made to date, but there are problems such as efficacy, side effects and emergence of resistant strains and the like, and safe and reliable eradication methods have not yet been established.

On the other hand, *Cinnamomum cassia* is a Ranunculales Lauraceae evergreen broad-leaved tree belonging to a dicotyledon and it is originated from China, and is distributed in Sri Lanka, Indochina and Korea (Jeju), and it is a medicinal use name of branches and bark of *Cinnamomum cassia* tree (Cinnamon tree) that grows up to about 8 m in height in mountain.

Regarding components or physiological activities of such *Cinnamomum cassia*, researches on antidiabetic effect (Boaduo N K et al., Pharm Biol. 2014, 52(6):756-61; Han Y et al., Pharm Biol. 2013, 51(8):961-7), infection prevention effect (Yeh C F et al., J Ethnopharmacol. 2013, 147(2):321-6), antioxidant action (Hwa J S et al., J Ethnopharmacol. 2012, 139(2):605-15), anti-stomach ulcer action of eugenol and cinnamic acid (Jung J et al., Yakugaku Zasshi. 2011, 131(7):1103-10), antifibrotic action (Lim C S et al., Biosci Biotechnol Biochem. 2010, 74(3):477-83), melanin synthesis inhibitory action (Kong Y H et al., Biol Pharm Bull. 2008, 31(5):946-8), osteogenesis promoting action (Lee K H et al., Phytother Res. 2006, 20(11):952-60), antibiosis (Ooi L S et al., Am J Chin Med. 2006, 34(3):511-22) and so on were known.

In this regard, Korean Patent Publication No. 10-2003-0030422 discloses a health supplementary food for improving stomach functions comprising the extract obtained by hot water extraction of *Alpiniae* semen, *Amomi* semen, *Cinnamomum cassia, Astragalus membranaceus* and *Citrus unshiu* peel at the ratio of 1:1:1:1 as an active ingredient.

On the other hand, cinnamic aldehyde which is the main component and the active ingredient of *Cinnamomum cassia* is easily oxidized and colored in air and therefore benzoic acid crystals may be educed, and thus it has been reported that the stability at the room temperature is low (Food Additives Codex, JongHee P et al, 2006), and 2-methoxycinnamic aldehyde has been also reported that the stability at the room temperature is low (Jeongsook L et al, 2013). Although these components of *Cinnamomum cassia* are known as index components, but it has been reported that there is risk that the stability of drugs are considerably degraded by these substances when preparing drugs from the *Cinnamomum cassia* extract comprising them.

Thus, the development of a preparation for preventing and treating gastritis and stomach ulcer which minimizes the ingredient content that may affect the stability and at the same time maximize the effectiveness has been still strongly required.

Lastly, it may be an important factor to reduce the dosage of the extract in a pharmaceutical composition. As reducing formulations such as tablets, syrup, and the like of drugs is considerably affected by the method for preparing the extract, it can be a core factor to reduce the size and volume of preparations in a lower volume than conventional common extract, and at the same time obtain the same effect, by selectively extracting the effective part.

Under these circumstances, the present inventors have tried to develop *Cinnamomum cassia* extract which has anti-ulcer efficacy through much excellent defensive factor increasing mechanisms compared to *Artemisia* extract preparation that is a commercially available herb medicine-based therapeutic agent for gastritis and stomach ulcer and shows much excellent pharmacological effects than the *Cinnamomum cassia* extract obtained by water extraction, alcohol extraction, solvent fractionation, and so on, or the extract prepared by *Cinnamomum cassia* single herb medicine. As a result, it was confirmed that when preparing extract by extracting with a specific solvent after pretreatment of a specific solvent to *Cinnamomum cassia* different from extraction, it exhibits an excellently enhanced gastritis or stomach ulcer preventing or treating effect than conventional extract and therefore not only it can effectively improve gastritis and peptic ulcer such as stomach ulcer, but also it can minimize components known to affect the stability such as cinnamic aldehyde and 2-methoxycinnamic aldehyde and the like and at the same time provide a preparation with very improved effectiveness, thereby completing the present invention.

DISCLOSURE

Technical Problem

An object of the present invention is to provide a composition comprising *Cinnamomum cassia* pretreated extract with an enhanced effect of preventing, improving or treating gastritis or stomach ulcer, a method for preventing, improving or treating gastritis or stomach ulcer using thereof, and a preparation method of the *Cinnamomum cassia* pretreated extract.

More specifically, one object of the present invention is to provide a pharmaceutical or food composition for preventing or treating gastritis or stomach ulcer comprising *Cinnamomum cassia* pretreated extract which is obtained by pretreating *Cinnamomum cassia* with a non-polar solvent and then extracting it with a polar solvent, a method for preventing, improving or treating gastritis or stomach ulcer using thereof, and a preparation method of the *Cinnamomum cassia* pretreated extract.

Technical Solution

One aspect to achieve the object, the present invention relates to a composition for preventing, improving or treating gastritis or peptic ulcer comprising *Cinnamomum cassia* pretreated extract which is obtained by pretreating *Cinnamomum cassia* with a non-polar solvent and extracting with a polar solvent, and a method for preventing, improving or treating gastritis or stomach ulcer using thereof.

The composition of the present invention may be a pharmaceutical composition or a food composition.

Advantageous Effects

The composition of the present invention comprises *Cinnamomum cassia* pretreated extract prepared through a unique process as an active ingredient, thereby not only showing excellent effects of stomach ulcer inhibition, mucosal amount improvement and inhibition of inflammation, but also minimizing cinnamic aldehyde and 2-methoxycinnamic aldehyde which may affect stability, to minimize stability hindrance factors, and it can provide a preparation in which problems such as toxicity, and so on are solved, as it is based on herb medicine, and therefore it has an excellent effect compared to conventional herb medicine-based drugs, and the size or dose of a formulation can be reduced due to properties showing the same effect with less dose, and thus it is useful for development of a preparation for prevention, improvement and treatment of gastritis or peptic ulcer.

BRIEF DESCRIPTION OF DRAWINGS

FIG. 1 is a photograph confirming the effect of inhibiting stomach damage of the composition according to the present invention, and FIG. 2 is a graph showing the effect of inhibiting stomach damage of the composition according to the present invention with a stomach ulcer index.

BEST MODE

Hereinafter, the present invention will be described in more detail.

The composition according to the present invention is characterized by comprising extract which is obtained by pretreating *Cinnamomum cassia* with a non-polar solvent and then extracting with a polar solvent as an active ingredient. *Cinnamomum cassia* used as crude herb medicine for the pretreated extract of the composition is a Ranunculales Lauraceae evergreen broad-leaved tree belonging to a dicotyledon and it is originated from China, and is distributed in Sri Lanka, Indochina and Korea (Jeju), and it means branches and bark of *Cinnamomum cassia* tree (Cinnamon tree) that grows up to about 8 m in height in mountain.

In the composition according to the present invention, the *Cinnamomum cassia* may be used as dried or cut in an appropriate size for extraction according to conventional known methods, and so on. In addition, the present invention is pretreated extract before extracting such *Cinnamomum cassia* crude herb medicine with a polar solvent, and such pretreatment means treatment with a non-polar solvent. For example, the non-polar solvent is characterized by being ethyl acetate, and a non-polar solvent up to 1 time to 3 times of solvent volume compared to the *Cinnamomum cassia* herb medicine weight may be used. As one preferable aspect, pretreatment may be performed by immersing and stirring sliced *Cinnamomum cassia* in the non-polar solvent like ethyl acetate for about 30 minutes to 3 hours at a range of 20 to 35° C., preferably, at a room temperature. During this pretreatment process, cinnamic aldehyde and 2-methoxycinnamic aldehyde that may adversely affect the stability may be effectively removed. Furthermore, the pretreated extract according to the present invention is characterized as polar solvent, preferably, water extract of *Cinnamomum cassia* pretreated as above. Extraction may be carried out at 80 to 100° C. for 2 hours to 6 hours, preferably 5 hours, by using about 6 times to 10 times volume, preferably 8 times volume of the polar solvent used for extraction compared to the *Cinnamomum cassia* herb medicine weight. This extraction may be performed once to several times, and the extracted pretreated extract may be further filtered, concentrated and dried, and methods used then may use filtering, concentration and drying methods commonly used for preparation of extract without limitations.

In one embodiment according to the present invention, *Cinnamomum cassia* was dried and sliced and was immersed and stirred at a room temperature over one hour by adding 2 times of ethyl acetate to *Cinnamomum cassia*, and after removing ethyl acetate, with water, pretreated *Cinnamomum cassia* herb medicine was washed, and water corresponding to 8 times of *Cinnamomum cassia* herb medicine was added and it was extracted at about 90° C. for 5 hours, and this was repeated twice. Accordingly, the collected extract was filtered, vacuum concentrated, vacuum dried or spray dried, to prepare *Cinnamomum cassia* ethyl acetate pretreated water extract.

The pharmaceutical composition of the present invention exhibits an excellent effect for preventing or treating gastritis or peptic ulcer like stomach ulcer and duodenum ulcer.

The pharmaceutical composition of the present invention may comprise the *Cinnamomum cassia* pretreated extract of 10 to 90% by weight based on the total weight of composition. This may be increased or decreased according to needs of users, and it may be increased or decreased appropriately according to circumstances such as dietary life, nutritive conditions, stomach inflammation or ulcer degree, progression of the disease, and the like.

The pharmaceutical composition may be administered orally or parenterally, and it may be used in a form of general drug preparations. Preferable pharmaceutical preparations include preparations for oral administration such as tablets, pills, powders, granules, hard or soft capsules, liquids, suspensions, and the like, and these pharmaceutical preparations may be prepared using a pharmaceutically acceptable common carrier, for example, in case of preparations for oral administration, excipients, binding agents, disintegrating agents, lubricants, solubilizers, suspending agents, preservatives or extenders and so on.

The dosage of the pharmaceutical composition of the present invention may be determined by an expert according to various factors such as conditions, age, body weight of patients, disease progression and the like, but generally 9.7~2,919 mg of extract a day may be administered once to several times as divided, and preferably, 29.2~2,919 mg, more preferably 68.1~2,919 mg may be administered. However, in case of a long-term intake, the amount may be the above range or less, and since the active ingredient has no problem in terms of stability, the amount over the above range may be used.

In addition, the composition of the present invention may be a food composition. The food may be health supplementary food, health functional food, functional food, and so on, but not limited thereto, and it includes natural food, processed food, general food materials and the like in which the *Cinnamomum cassia* pretreated extract of the present invention is added. Herein functionality means obtaining a useful effect for health care uses like nutrient control or physiological actions for the structure and function of a human body. The health supplementary food, health functional food or functional food of the present invention may be prepared by methods commonly used in the art, and during the preparation, it may be prepared by adding raw materials and components commonly added in the art. Moreover, different from general drugs, it has an advantage of no side effects which may be caused in case of long-term use of drugs, since it uses herb medicine fed currently as raw materials, and it has outstanding portability, and therefore the health functional food of the present invention can be ingested as an adjuvant for increasing the effect of preventing or improving gastritis or stomach ulcer. The mixed amount of active ingredients may be suitably determined according to use purposes (prevention, health or therapeutic treatment). Generally, 10 to 90% by weight of the *Cinnamomum cassia* pretreated extract according to the present invention may be comprised during food preparation. In case of long-term ingestion on purpose of health control, the amount may be used in the above range or less.

The effective dose may be used following the effective dose of the pharmaceutical composition, but in case of long-term ingestion for improvement or maintenance of gastritis or stomach ulcer, it may be the above range or less, and the effective ingredients may be used over the above range, as they are herb medicine components and have no problem in terms of stability.

There is no particular limitation on the kind of the food. The food composition comprising the *Cinnamomum cassia* pretreated extract may be used in a form of preparations for oral administration such as tablets, hard or soft capsules, liquids, suspensions, and the like, and these preparations may further comprise an acceptable food supplementary additive. The term "food supplementary additive" is added for preparing each formulation of health functional food, and it may be selected appropriately by those skilled in the art can select and used. Examples of the food supplementary additive include various nutritional supplements, vitamins, minerals (electrolytes), flavors such as synthetic flavors and natural flavors and the like, coloring agents and fillers, pectic acid and its salt, alginic acid and its salt, organic acids, protective colloid thickeners, pH adjusting agents, stabilizers, preservatives, glycerin, alcohol, carbonating agents used for carbonated beverages, and so on, but the kind of the food supplementary additive of the present invention is not limited by these examples.

In addition, the food composition comprising the *Cinnamomum cassia* pretreated extract of the present invention may be added by itself or used with other food or food composition, and may be appropriately used according to common methods. The mixed amount of effective ingredients may be suitably determined according to its use purposes (prevention, improvement or therapeutic treatment).

Examples of the food in which the *Cinnamomum cassia* pretreated extract may be added are meat, sausage, bread, chocolate, candies, snack, confectionery, pizza, ramen, other noodles, gum, dairy products including ice cream, various kinds of soup, beverages, tea, drinks, alcohol beverages and vitamin complex, other nutritional supplements, and the like, but is not limited by these kinds of food.

Furthermore, as another aspect, the present invention relates to a preparation method of the *Cinnamomum cassia* pretreated extract according to the present invention comprising the following steps:

a) a step of pretreating *Cinnamomum cassia* by immersing it in a non-polar solvent;

b) a step of removing the non-polar solvent in the step a); and c) a step of extracting the *Cinnamomum cassia* collected in the step b) with a polar solvent.

The non-polar solvent used in the step a) of the preparation method is characterized by being ethyl acetate, and a non-polar solvent up to 1 time to 3 times of solvent volume compared to the *Cinnamomum cassia* herb medicine may be used. As one preferable aspect, pretreatment may be performed by immersing and stirring sliced *Cinnamomum cassia* in the non-polar solvent like ethyl acetate for about 30 minutes to 3 hours at a range of 20 to 35° C., preferably, at a room temperature. During this pretreatment process, cinnamic aldehyde and 2-methoxycinnamic aldehyde that may adversely affect the stability may be effectively removed.

The step b) is a step of removing the non-polar solvent from the *Cinnamomum cassia* pretreated with the non-polar solvent and known methods for removing a non-polar solvent may be used without limitations.

The step c) may be performed by extracting at 80 to 100° C. for 2 hours to 6 hours, preferably 5 hours, using about 6 times to 10 times, preferably 8 times of weight compared to *Cinnamomum cassia* herb medicine. Such a step c) may be performed once to several times.

As an additional aspect, the pretreated extract prepared in the step c) may be filtered, concentrated and dried, and for methods used then, filtering, concentration and drying methods commonly used for preparation of extract may be used without limitations. In one specific aspect, when preparing the *Cinnamomum cassia* pretreated extract by the preparation method according to the present invention, the yield is 15 to 20→1 (meaning that 1 Kg of the final extraction dry ex is obtained when adding 15 to 20 Kg of crude herb medicine).

According to one example of the present invention, the *Cinnamomum cassia* pretreated extract prepared according to the preparation method of the present invention not only exhibits excellent effects of stomach ulcer inhibition, stomach mucosal amount improvement and inhibition of inflammation, but also exhibits an enhanced effect of minimizing cinnamic aldehyde and 2-methoxycinnamic aldehyde which may affect stability, to minimize stability hindrance factors, compared to a conventional herb medicine-based therapeutic agent for gastritis and stomach ulcer, *Artemisia* extract preparation, as well as simple water extract of *Cinnamomum cassia* and extract in which *Cinnamomum cassia* is pretreated with other solvent.

MODE FOR INVENTION

Hereinafter, the present invention will be described in detail by examples. However, the following examples are intended to illustrate the present invention only, and the present invention is not limited by the following examples.

Example 1. Preparation of *Cinnamomum cassia* Pretreated Extract According to the Present Invention The *Cinnamomum cassia* pretreated extract according to the present invention was prepared as follows. Specifically, 2 times of ethyl acetate was added to *Cinnamomum cassia* herb medicine and it was immersed and stirred at a room temperature for over 1 hour. After removing ethyl acetate and washing *Cinnamomum cassia* herb medicine with water, 8 times of water was added and it was extracted at near about 90° C. for 5 hours (2 repeats). The *Cinnamomum cassia* pretreated water extract was prepared by filtering, vacuum concentrating, vacuum drying or spray drying the extract (extract yield: 15~20→1).

Comparative Examples 1 to 6. Preparation of *Cinnamomum cassia* Solvent Extract, *Cinnamomum cassia* Pretreated Extract Using Other Solvent and Commercial Preparations For comparison with the *Cinnamomum cassia* pretreated extract according to the present invention, *Cinnamomum cassia* solvent extract and *Cinnamomum cassia* butanol pretreated extract, and Ranitidine, Rebamipide and *Artemisia* extract as commercial preparations were prepared.

1) *Cinnamomum cassia* Ethanol Extract

To *Cinnamomum cassia* herb medicine, 8 times of ethanol was added and it was extracted at near about 90° C. for 5 times (2 repeats). The extract was filtered, vacuum concentrated, vacuum dried or spray dried to use it as *Cinnamomum cassia* ethanol extract (extract yield: 25→1).

2) *Cinnamomum cassia* Water Extract

The extract was prepared by the same method with the *Cinnamomum cassia* ethanol extract, but only the extraction solvent was changed into water (extract yield: 11~13→1).

3) *Cinnamomum cassia* Butanol Pretreated Water Extract

The extract was prepared by the same method with the Example 1, but only the pretreatment solvent was changed into butanol.

Only the main ingredients of commercial preparations of Ranitidine, Rebamipide, and *Artemisia* extract were used.

TABLE 1

| Kinds of comparative preparations | |
|---|---|
| Comparative example | Ingredient name |
| Comparative example 1 | *Cinnamomum cassia* ethanol extract |
| Comparative example 2 | *Cinnamomum cassia* water extract |
| Comparative example 3 | *Cinnamomum cassia* butanol pretreated water extract |
| Comparative example 4 | Ranitidine |
| Comparative example 5 | Rebamipide |
| Comparative example 6 | *Artemisia* extract |

Experimental Example 1. Confirmation of Inhibition Rate of Stomach Ulcer

In order to confirm the inhibition rate of stomach ulcer of the Example 1 and Comparative examples 1 to 6, the test was carried out according to the following method.

Test animals were randomly assigned to 10 animals of specific pathogen free (SPF) 7-week-old rat males per group so that the average body weight was maximally uniformly distributed throughout the adaptation period (7 days). The administration route was single oral administration of substances of the Example 1 and Comparative examples 1 to 6, respectively, and the dose was calculated to be 10 mL/Kg on the basis of the weight measured on the day of administration. All animals were fasted 48 hours before administration of test substances and control drug, and then each of test substances and control drug was orally administered, and Indomethacin previously prepared 30 minutes after administration was orally administered at a dose of 80 mg/kg. After anesthetizing with diethyl ether 5 hours after administration of Indomethacin, stomach was removed and the gastric mucosa was photographed with a digital camera. The area of the damaged site was analyzed using ImageJ software (NIH, Bethesda, MD). The stomach ulcer index was measured according to the following Equation 1. The result was shown in the following Table 2, FIG. 1 and FIG. 2.

$$\text{Stomach ulcer index (\%)} = (\text{damage area/total area}) \times 100 \qquad [\text{Equation 1}]$$

TABLE 2

Inhibition rate of stomach ulcer compared to the induced group

| Group | Dose(mg/kg) | Stomach ulcer index (%) | Inhibition rate (%), compared to the induced group |
|---|---|---|---|
| Induced group | 0 | 6.58 ± 1.60 | — |
| Comparative example 2 | 150.0 | 2.00 ± 1.05* | 69.6 |
| Comparative example 3 | 150.0 | 2.88 ± 2.29* | 56.2 |
| Comparative example 4 | 75.0 | 0.20 ± 0.29* | 97.0 |
| Comparative example 6 | 150.0 | 2.35 ± 1.83* | 64.3 |
| Example 1 | 150.0 | 0.24 ± 0.18* | 96.4 |

*showing significant difference compared to the induced group ($p < 0.05$)

As could be seen in Table 2, FIG. 1 and FIG. 2, the *Cinnamomum cassia* ethyl acetate pretreated water extract of Example 1 according to the present invention exhibited the 27.4 to 40.0% increased inhibition rate, compared to not only the simple solvent extract of *Cinnamomum cassia* (Comparative example 2), but also the extract which was obtained by pretreating *Cinnamomum cassia* with butanol and extracting with water (Comparative example 3). Moreover, it could be confirmed that this was the equivalent level of inhibition rate to the strong stomach ulcer inhibitor, Ranitidine (Comparative example 4). It could be seen that the rat effective does of Example 1 (150 mg/kg) was 1,460 mg when converted into the dose per body weight 60 Kg adult unit area.

Experimental Example 2. Confirmation of Effect of Improving Mucosal Amount

In order to confirm the effect of improving the mucosal amount of the Example 1 and Comparative examples 1 to 6, the test was carried out according to the following method.

Test animals were randomly assigned to 10 animals of specific pathogen free (SPF) 7-week-old rat males per group so that the average body weight was maximally uniformly distributed throughout the adaptation period (7 days). All animals were fasted 48 hours before administration and then test substances and control drug were orally administered, and 30 minutes after administration, Indomethacin 80 mg/kg was orally administered. It was anesthetized with diethyl ether 7 hours after administration of Indomethacin and blood was collected from postcaval vein, and then stomach was removed and was incised along with greater curvature and was turned over and the glandular ventriculus mucosal surface was exposed outside and the glandular ventriculus was washed out with 0.25 M sucrose solution. After soaking in 0.1% w/v alcian blue 8 GX solution 15 mL for 2 hours, it was washed with 15 mL of 0.25 M sucrose solution twice (15 minutes each) to remove excessive amount of dye. To extract a reagent combined with stomach mucus, the stomach tissue was soaked in 15 mL of 0.5 M $MgCl_2$ solution for 2 hours and shaking was carried out intermittently for 1 minute each at intervals of 30 minutes. After mixing the extract solution with diethyl ether in the same amount and shaking, it was centrifuged at 3,500 rpm for 10 minutes and for the supernatant, the absorbance was measured at 605 nm. 0.1% w/v alcian blue 8 GX solution was diluted with 0.25 M sucrose solution and standard solution was prepared and thereby a standard curve was fabricated and the measured absorbance value was converted into the amount of alcian blue combined with the stomach mucus, and the result was shown in Table 3.

TABLE 3

Confirmation of the effect of improving mucosal amount

| Group | Dose(mg/kg) | Mucosal amount [µg/L] | % compared to the normal group |
|---|---|---|---|
| Normal group | — | 11.2 ± 2.6 | 100 |
| Induced group | — | 4.8 ± 1.9 | 42.9 |
| Comparative example 2 | 300.0 | 8.0 ± 2.1* | 72.0 |
| Comparative example 5 | 100.0 | 10.6 ± 3.7* | 94.6 |
| Comparative example 6 | 300.0 | 8.5 ± 2.4* | 76.4 |
| Example 1 | 300.0 | 9.1 ± 2.7* | 81.3 |

*showing significant difference compared to the induced group ($p < 0.05$)

As could be seen in the Table 3, the *Cinnamomum cassia* ethyl acetate pretreated water extract according to the present invention of Example 1 exhibited 10% increased stomach mucus amount compared to the simple *Cinnamomum cassia* water extract (Comparative example 2). In addition, it was confirmed that such an effect of increasing the stomach mucus amount was increased compared to the commercially available herb medicine preparation, *Artemisia* extract (Comparative example 6). It could be seen that the rat effective does of Example 1 (300 mg/kg) was 2,919 mg when converted into the dose per body weight 60 Kg adult unit area.

Experimental Example 3. Confirmation of Effect of Improvement of PGE2

Since the recovery mechanism of stomach mucous membrane blood stream and epithelial cells is maintained and the action of preserving cells of the stomach mucous membrane was shown, when PGE2 in serum is increased, the enhanced improvement of PGE2 affects treatment of gastritis or stomach ulcer. In order to confirm the effect of the Example 1 and Comparative examples 2, 5 to 6 according to the present invention for this improvement of PGE2, for the blood collected in Test example 2, serum was separated according to the protocol provided by the manufacturer of PGE2 ELISA Kit and then sampling treatment was carried out, and then it was analyzed, and the result was shown in the following Table 4.

TABLE 4

PGE2 improvement effect

| Group | Dose(mg/kg) | PGE2 [ng/mL] | % compared to the normal group |
|---|---|---|---|
| Normal group | — | 1.88 ± 0.2 | 100 |
| Induced group | — | 1.61 ± 0.17 | 0 |
| Comparative example 2 | 300.0 | 1.78 ± 0.2* | 64.4 |
| Comparative example 5 | 100.0 | 1.82 ± 0.14* | 77.7 |
| Comparative example 6 | 300.0 | 1.73 ± 0.39 | 44 |
| Example 1 | 300.0 | 1.8 ± 0.19* | 72.6 |

*showing significant difference compared to the induced group ($p < 0.05$)

As could be confirmed in Table 4, the *Cinnamomum cassia* ethyl acetate pretreated water extract according to the present invention (Example 1) exhibited the very enhanced PGE2 improving effect compared to the simple *Cinnamomum cassia* solvent extract (Comparative example 2), and exhibited the even about 28% increased improvement rate compared to the commercially available herb medicine, *Artemisia* extract (Comparative example 6), and exhibited the equivalent level of effect to the strong stomach ulcer therapeutic agent, Rebamipide (Comparative example 5).

Experimental Example 4. Stomach Ulcer Inhibition Rate by Volume

The stomach ulcer test by volume for the Example 1 was tested by the method as Experimental example 1, and was shown in Table 5.

TABLE 5

Inhibition rate of stomach ulcer by dose

| Group | Dose(mg/kg) | Stomach ulcer index (%) | Inhibition rate (%), compared to the induced group |
|---|---|---|---|
| Induced group | 0 | 5.03 ± 1.17 | 0.0 |
| Example 1 | 1 | 3.61 ± 0.86* | 28.1 |
| Example 1 | 3 | 2.18 ± 1.21* | 56.6 |
| Example 1 | 7 | 1.46 ± 0.70* | 70.9 |
| Example 1 | 15 | 1.03 ± 0.63* | 79.5 |
| Example 1 | 25 | 0.77 ± 0.53* | 84.7 |
| Example 1 | 50 | 0.48 ± 0.29* | 90.4 |
| Example 1 | 100 | 0.24 ± 0.22* | 95.3 |
| Example 1 | 150.0 | 0.24 ± 0.18* | 96.4 |
| Comparative example 2 | 150.0 | 2.00 ± 1.05* | 69.6 |

*showing significant difference compared to the induced group ($p < 0.05$)

As could be confirmed in Table 5, the *Cinnamomum cassia* ethyl acetate pretreated water extract according to the present invention (Example 1) exhibited the significant stomach ulcer inhibition effect from 1 mg/kg up to 150 mg/kg to the maximum. It could be seen that the rat effective does was 1,460 mg to the maximum at 9.7 mg (converted volume of rat 1 mg/kg), when converted into the dose per body weight 60 Kg adult unit area.

In addition, Comparative example 2 (conventional (or common) *Cinnamomum cassia* water extract) exhibited the inhibition rate of 69.6% compared to the induced group at 150 mg/kg and it was shown that the similar effect to the volume of 7 mg/kg of Example 1 of the present invention was exhibited, and therefore it could be seen that the same efficacy was exhibited even when reducing about 21 times of volume.

Experimental Example 5. Analysis of Content of *Cinnamomum cassia* Pretreated Extract According to the Present Invention In order to analyzed the components and contents of the *Cinnamomum cassia* pretreated extract according to the present invention, for the *Cinnamomum cassia* extract of Example 1, HPLC content analysis was conducted under the following conditions using cinnamic acid, cinnamic aldehyde, 2-methoxy cinnamic aldehyde standard products.

HPLC equipment operating conditions
1) Column Kromasil 100-5 $C_{18}$ (4.6 mm×150 mm, 5.0 μm) or column equivalent to the same
2) Detector: Ultraviolet spectrophotometer (measurement wavelength: 280 nm)
3) Flow rate: About 0.7 mL/minute
4) Dose: 10 μL
5) Mobile phase: Acetonitrile (0.2% trifluoroacetic acid)/purified water The result was shown in Table 6.

TABLE 6

HPLC content analysis

| | Cinnamic acid | Cinnamic aldehyde | 2-methoxy cinnamic aldehyde |
|---|---|---|---|
| Comparative example 1 | 2.91 | 22.3 | 3.53 |
| Comparative example 2 | 5.61 | 0.3 | 0.44 |
| Example 1 | 4.26 | 0.07 | 0.13 |

[Unit: mg/g]

Cinnamic aldehyde which is the main component and the active ingredient of *Cinnamomum cassia* is easily oxidized and colored in air and therefore benzoic acid crystals may be educed, and thus it has been reported that the stability at the room temperature is low (Food Additives Codex, JongHee P et al, 2006), and 2-methoxycinnamic aldehyde has been also reported that the stability at the room temperature is low (Jeongsook L et al, 2013). However, as could be confirmed in Table 5, it was confirmed that the *Cinnamomum cassia* pretreated extract according to the present invention comprised very small amount of the cinnamic aldehyde and 2-methoxycinnamic aldehyde compared to the *Cinnamomum cassia* ethanol, *Cinnamomum cassia* water extract that *Cinnamomum cassia* was extracted simply with a solvent. Cinnamic aldehyde was reduced about 323 times for Comparative example 1 and about 4.3 times for Comparative example 2, and 2-methoxycinnamic aldehyde was reduced about 27 times for Comparative example 1 and about 3.4 times for Comparative example 2. Thus, the *Cinnamomum cassia* pretreated extract according to the present invention minimized components capable of affecting the stability.

The invention claimed is:

1. A preparation method of *Cinnamomum cassia* extract comprising a) a step of immersing *Cinnamomum cassia* into ethyl acetate to reduce cinnamic aldehyde and 2-methoxycinnamic aldehyde in the extract; b) a step of removing the ethyl acetate in the step a); and c) a step of extracting *Cinnamomum cassia* obtained in the step b) with water,
   wherein the step a) is performed by immersing *Cinnamomum cassia* into ethyl acetate having a weight of 1 to 3 times compared to *Cinnamomum cassia* herb medicine and stirring at 20 to 35° C. for 30 minutes to 3 hours, and
   wherein the step c) is performed by extracting *Cinnamomum cassia* obtained in the step b) for 80 to 100° C. for 2 hours to 6 hours using water of 6 times to 10 times compared to *Cinnamomum cassia* herb medicine.

* * * * *